United States Patent
Wei et al.

(10) Patent No.: US 8,027,724 B2
(45) Date of Patent: Sep. 27, 2011

(54) HYPERTENSION DIAGNOSIS AND THERAPY USING PRESSURE SENSOR

(75) Inventors: Xuan Wei, Plymouth, MN (US); Cheng Zhang, Vadnais Heights, MN (US); Shantha Arcot-Krishnamurthy, Roseville, MN (US); Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 538 days.

(21) Appl. No.: 11/833,435

(22) Filed: Aug. 3, 2007

(65) Prior Publication Data

US 2009/0036940 A1 Feb. 5, 2009

(51) Int. Cl.
*A61N 1/08* (2006.01)

(52) U.S. Cl. .......................................... 607/23; 600/485
(58) Field of Classification Search .............. 607/17–19, 607/23, 30, 32, 44, 60, 62; 600/485–505
See application file for complete search history.

(56) References Cited

U.S. PATENT DOCUMENTS

| | | | |
|---|---|---|---|
| 5,334,222 A | 8/1994 | Salo et al. | |
| 5,626,623 A | 5/1997 | Kieval et al. | |
| 5,954,752 A | 9/1999 | Mongeon et al. | |
| 6,628,989 B1 | 9/2003 | Penner et al. | |
| 6,708,061 B2 | 3/2004 | Salo et al. | |
| 6,764,446 B2 | 7/2004 | Wolinsky et al. | |
| 6,865,419 B2 | 3/2005 | Mulligan et al. | |
| 7,024,248 B2 | 4/2006 | Penner et al. | |
| 7,209,786 B2 | 4/2007 | Brockway et al. | |
| 7,273,457 B2 | 9/2007 | Penner | |
| 2003/0004421 A1* | 1/2003 | Ting et al. ..................... | 600/485 |
| 2004/0172083 A1* | 9/2004 | Penner ............................ | 607/35 |
| 2004/0260374 A1 | 12/2004 | Zhang et al. | |
| 2005/0149129 A1 | 7/2005 | Libbus et al. | |
| 2005/0149143 A1 | 7/2005 | Libbus et al. | |
| 2005/0222640 A1 | 10/2005 | Schwartz et al. | |
| 2005/0234517 A1 | 10/2005 | Braunschweig et al. | |
| 2006/0079793 A1* | 4/2006 | Mann et al. .................... | 600/486 |
| 2006/0167359 A1* | 7/2006 | Bennett et al. ................ | 600/485 |
| 2007/0088221 A1* | 4/2007 | Stahmann ...................... | 600/485 |
| 2007/0100242 A1* | 5/2007 | Sawanoi et al. ............... | 600/485 |
| 2007/0129765 A1 | 6/2007 | Gilkerson et al. | |
| 2007/0162090 A1* | 7/2007 | Penner ............................ | 607/60 |
| 2007/0191904 A1 | 8/2007 | Libbus et al. | |
| 2007/0260285 A1 | 11/2007 | Libbus et al. | |
| 2008/0071185 A1 | 3/2008 | Beck et al. | |
| 2008/0243016 A1 | 10/2008 | Liao et al. | |

OTHER PUBLICATIONS

Davies, I.B., Editorials: Chronic Hypotension, 1982, Journal of the Royal Society of Medicine, vol. 75, pp. 577-580.*

* cited by examiner

*Primary Examiner* — Kennedy J Schaetzle
*Assistant Examiner* — Erica Lee
(74) *Attorney, Agent, or Firm* — Schwegman, Lundberg & Woessner, P.A.

(57) ABSTRACT

An example relates to a method for sensing a pulmonary artery pressure (PAP) and providing a sensed PAP signal, detecting an abnormal blood pressure (BP) condition using information from the sensed PAP signal, delivering a pacing energy to a heart, and automatically altering at least one pacing characteristic in response to the detected abnormal BP condition. The detecting an abnormal BP condition can include detecting various forms of hypertension or hypotension. The automatically altering the at least one pacing characteristic can include automatically altering at least one of a pacing rate, a pacing waveform, an atriventricular (AV) delay, an interventricular (VV) delay, a pacing mode, or a pacing site. The method can also include delivering vagal nerve stimulation and automatically altering the vagal nerve stimulation in response to the detected abnormal BP condition. The detecting the abnormal BP condition can also include using a sensed auxiliary physiological parameter.

31 Claims, 6 Drawing Sheets

HYPERTENSION DIAGNOSIS AND THERAPY USING PRESSURE SENSOR

TECHNICAL FIELD

This document pertains generally to hypertension diagnosis and therapy, and more particularly, but not by way of limitation, to hypertension diagnosis and therapy using a pulmonary artery pressure sensor.

BACKGROUND

A chronic electrical stimulator, such as a cardiac stimulator, can be implanted to deliver medical therapy. Examples of cardiac stimulators include implantable cardiac rhythm management (CRM) device such as pacemakers, implantable cardiac defibrillators (ICDs), and implantable devices capable of performing pacing and defibrillating functions.

A CRM device, such as an implantable pacemaker, is typically an implantable device that can provide electrical stimulation to selected chambers of the heart in order to treat disorders of cardiac rhythm. In an example, the implantable pacemaker is a CRM device that can pace the heart with timed pacing pulses, thereby establishing an appropriate cardiac rhythm, such as by enforcing a minimum heart rate, in order to meet a metabolic demand. In an example, the CRM device can deliver synchronized pacing pulses to different areas of the heart in order to coordinate contractions. Coordinated contractions can allow the heart to pump efficiently while providing sufficient cardiac output.

Heart failure generally refers to a clinical syndrome in which cardiac function causes a below normal cardiac output that can fall below a level adequate to meet the metabolic demand of peripheral tissues. Heart failure can present itself as congestive heart failure (CHF) due to the accompanying venous and pulmonary congestion. Heart failure can be due to a variety of etiologies such as ischemic heart disease.

Blood pressure generally refers to the force exerted on the walls of blood vessels by circulating blood, and can be indicative of the amount of work that the heart must do in order to circulate blood through the circulatory system of a subject. Hypertension generally refers to an elevated blood pressure, whereas hypotension generally refers to a low blood pressure.

Hypertension is a cause of heart disease and other related cardiac co-morbidities. Hypertension can occur when blood vessels constrict. As a result, the heart works harder to maintain flow at a higher blood pressure, which can contribute to heart failure. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Hypotension can be indicative of various physiological states, such as: a reduced blood volume, which can result from a loss of blood or other fluids; a decreased cardiac output, which can result from CHF, myocardial infarction (MI), or a low heart rate; or excessive vasodilation or insufficient constriction of the resistance blood vessels due to decreased sympathetic nervous system output or increased parasympathetic activity.

SUMMARY

An example relates to a method for sensing a pulmonary artery pressure (PAP) and providing a sensed PAP signal, detecting an abnormal blood pressure (BP) condition using information from the sensed PAP signal, delivering a pacing energy to a heart, and automatically altering at least one pacing characteristic in response to the detected abnormal BP condition. The detecting an abnormal BP condition can include detecting various forms of hypertension or hypotension. The automatically altering the at least one pacing characteristic can include automatically altering at least one of a pacing rate, a pacing waveform, an atriventricular (AV) delay, an interventricular (VV) delay, a pacing mode, or a pacing site. The method can also include delivering vagal nerve stimulation and automatically altering the vagal nerve stimulation in response to the detected abnormal BP condition. The detecting the abnormal BP condition can also include using a sensed auxiliary physiological parameter.

A system example includes an implantable PA pressure sensor, a diagnostic circuit, and an implantable PG. The implantable PA pressure sensor is configured to sense a PAP and provide a sensed PAP signal. The diagnostic circuit is configured to detect an abnormal BP condition using information from the sensed PAP signal. The implantable PG is configured to deliver a pacing energy to a heart and automatically alter at least one pacing characteristic in response to the detected abnormal BP. The abnormal BP condition can include various forms of hypertension or hypotension. The at least one pacing characteristic can include at least one of a pacing rate, a pacing waveform, an atriventricular (AV) delay, an interventricular (VV) delay, a pacing mode, or a pacing site. In an example, the system can include an auxiliary physiological sensor configured to sense an auxiliary physiological parameter different than the PAP and provide a sensed auxiliary physiological signal. The diagnostic circuit can be configured to detect an abnormal BP condition using information from the sensed PAP signal and information from the sensed auxiliary physiological signal.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
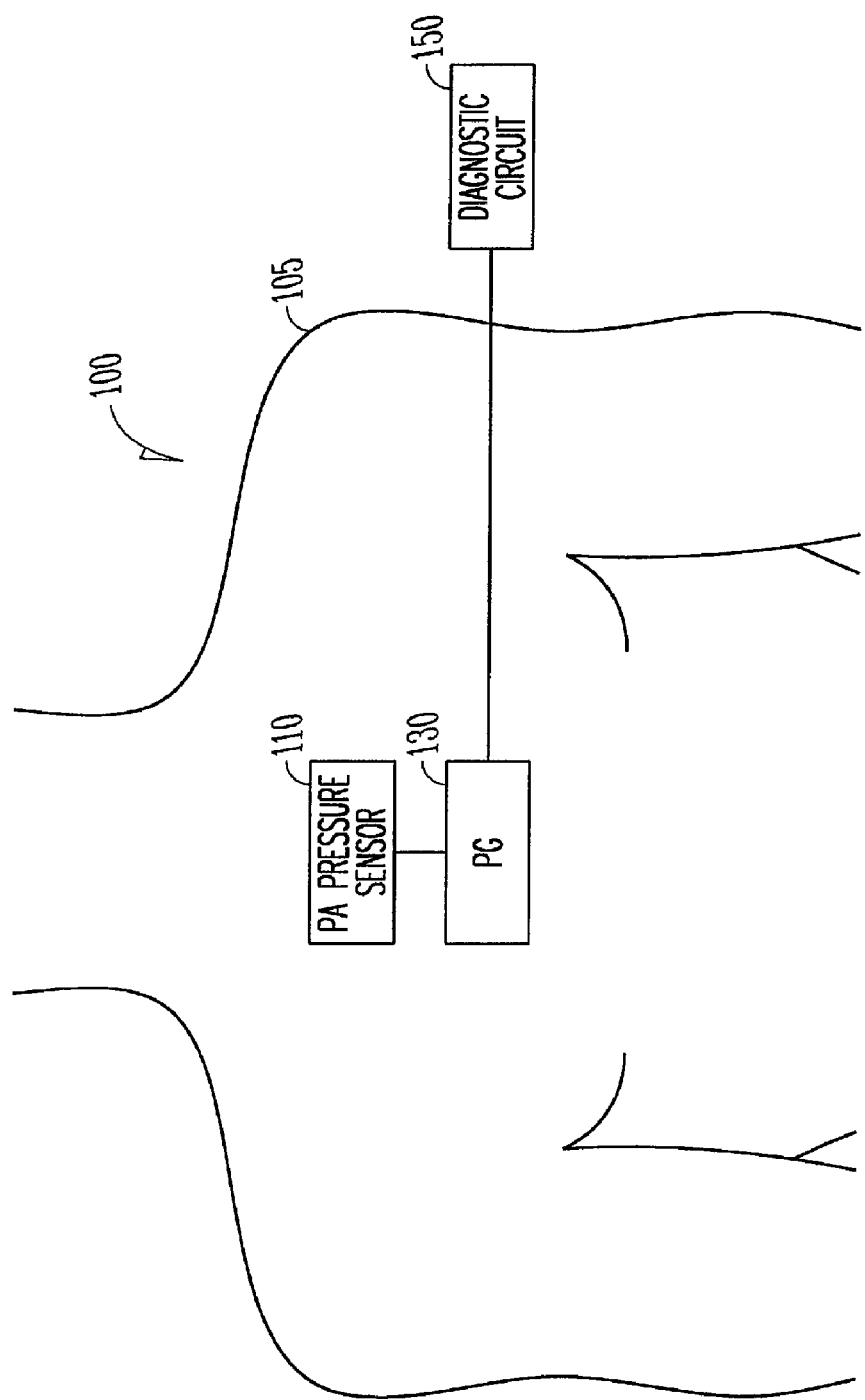
FIG. 1 illustrates generally an example of a system including a pulmonary artery (PA) pressure sensor, a pulse generator (PG), and a diagnostic circuit.

FIG. 1 illustrates generally an example of a system 100 including a pulmonary artery (PA) pressure sensor 110, a pulse generator (PG) 130, and a diagnostic circuit 150. The PA pressure sensor 110 generally includes an implantable PA pressure sensor configured to be located in a PA of a subject 105. In certain examples, the PG 130 or the diagnostic circuit 150 can be either an implantable component or an external component, or the PG 130 or the diagnostic circuit 150 can be a combination of implantable and external components. In an example, at least some of the functionality of the diagnostic circuit 150 can be implemented using the PG 130.

The PA pressure sensor 110 can be used to monitor a parameter associated with the performance of the heart, including collecting information pertaining to a pressure or a flow of blood within the PA, such as a pulmonary artery pressure (PAP) of the subject 105. Generally, the PAP of the subject can be correlative or indicative of the left ventricular pressure (LVP) of the subject 105, and thus, can provide a better indication of cardiac performance than other blood pressure sensors, such as external blood pressure sensors (e.g., inflatable cuff blood pressure monitors) or other implantable pressure sensors located farther from the left side of the heart. In an example, the PA pressure sensor 110 can include a lead-based pressure sensor (e.g., a pressure sensor coupled to a lead, catheter, or stent-like fixture) placed within the PA of the subject 105. However, for chronic long-term monitoring (e.g., monitoring greater or much greater than 24 hours), or for a combination of long-term monitoring and short-term monitoring, a non lead-based pressure sensor (e.g., a pressure sensor fixed to bodily tissue or other bodily structure, without being coupled to a lead, that can communicate with other devices wirelessly) may be preferred. Thus, in other examples, the PA pressure sensor 110 can include a non lead-based chronic PA pressure sensor, fixed to a location within the PA. By using an implantable PA pressure sensor, long-term monitoring of the pressure within the PA can be accomplished.

In an example, the PA pressure sensor 110 can be configured to provide a sensed PAP signal, such as an electrical sensed PAP signal, a mechanical sensed PAP signal, or an optical sensed PAP signal that includes information about the PAP of the subject 105. The PA pressure sensor 110 can be configured to transmit PA information, such as the sensed PAP signal, to other implantable or external medical devices, such as the PG 130 or the diagnostic circuit 150.

In the example of FIG. 1, the PG 130 can be communicatively coupled to the PA pressure sensor 110, and the diagnostic circuit 150 can be communicatively coupled to the PG 130. In other examples, the diagnostic circuit 150 can be communicatively coupled to the PA pressure sensor 110, or at least some of the functionality of the diagnostic circuit 150 can be implemented using the PG 130. In an example, the PG 130 can be configured to receive information from the PA pressure sensor 110. In certain examples, the diagnostic circuit 150 can be configured to receive information from the PG 130, such as information from the PA pressure sensor 110, or the diagnostic circuit 150 can be configured to receive information directly from the PA pressure sensor 110.

The PG 130 can be configured to deliver a pacing energy, or other electrical stimulation signal adapted to provide a cardiac stimulation therapy, to a heart. In an example, the PG 130 can be configured to deliver the pacing energy to the heart using at least one pacing characteristic, such as a pacing rate, a pacing waveform, an atrioventricular (AV) delay, an interventricular (VV) delay, a pacing mode, or a pacing site. In certain examples, the pacing characteristic includes the pacing rate. In other examples, the pacing characteristic includes the pacing rate and the pacing mode. In an example, the PG 130 can also include a neural stimulator configured to deliver a vagal nerve stimulation signal adapted to provide a neural stimulation therapy.

The diagnostic circuit 150 can be configured to detect an abnormal blood pressure (BP) condition, such as by using information from the sensed PAP signal. The abnormal BP condition can include hypertension, hypotension, or other BP conditions. In an example, hypertension can include at least one of chronic hypertension, transient hypertension, nocturnal hypertension, circadian hypertension, systolic hypertension, diastolic hypertension, or other types of hypertension. In certain examples, hypertension includes nocturnal hypertension. In other examples, hypertension includes chronic hypertension and systolic hypertension. In an example, hypotension can include at least one of chronic hypotension, transient hypotension, circadian hypotension, or other types of hypotension.

In an example, the diagnostic circuit 150 can include an external programmer, or a combination of a repeater, router, or other communication device and an external programmer or other processor.

Figure 2:
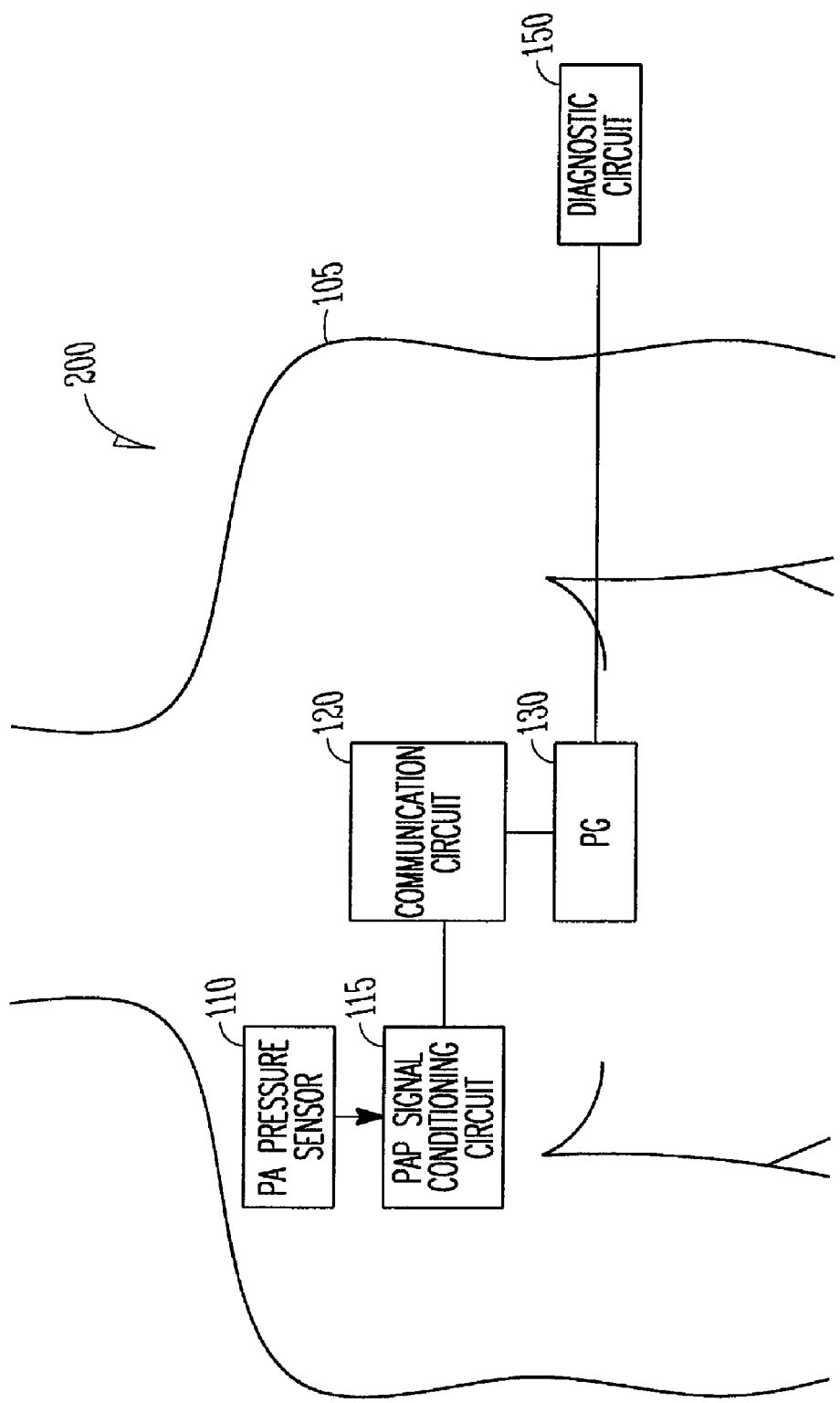
FIG. 2 illustrates generally an example of a system including a pulmonary artery pressure (PAP) signal conditioning circuit and a communication circuit.

FIG. 2 illustrates generally an example of a system 200 including a pulmonary artery pressure (PAP) signal conditioning circuit 115 and a communication circuit 120. The PAP signal conditioning circuit 115 can be coupled to the PA pressure sensor 110 and can be configured to condition information from the PA pressure sensor 110, such as the sensed PAP signal, into a conditioned PAP signal, such as for transmission to an implantable or external medical device. The communication circuit 120 can be coupled to the PAP signal conditioning circuit 115, and can be configured to receive information from the PAP signal conditioning circuit 115, such as the conditioned PAP signal.

In an example, the communication circuit 120 can be communicatively coupled to the PG 130, and can be configured to transmit PAP information, such as the conditioned PAP signal, to the PG 130. In certain examples, the communication circuit 120 can transmit PAP information to the PG 130 wirelessly, such as through a radio frequency (RF) communication or other wireless connection. In other examples, the communication circuit 120 can be configured to transmit PAP information to other medical devices, such as the diagnostic circuit 150.

Figure 3:
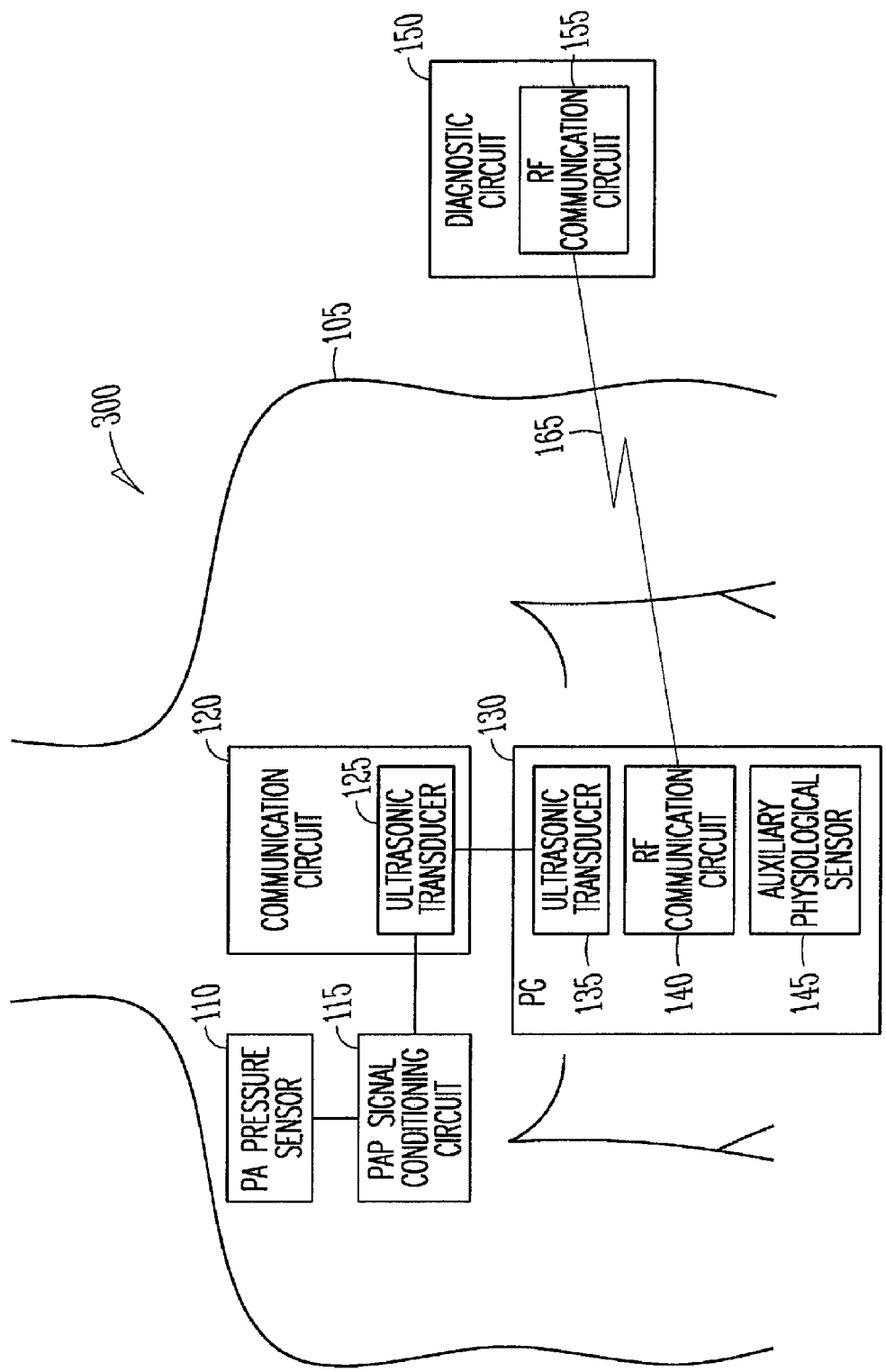
FIG. 3 illustrates generally an example of a system including a communication circuit having an ultrasonic transducer, a PG having an ultrasonic transducer, a radio frequency (RF) communication circuit, and an auxiliary physiological sensor, and a diagnostic circuit having an RF communication circuit.

FIG. 3 illustrates generally an example of a system 300 including a communication circuit 120 having an ultrasonic transducer 125, a PG 130 having an ultrasonic transducer 135, a radio frequency (RF) communication circuit 140, an auxiliary physiological sensor 145, and a diagnostic circuit 150 having an RF communication circuit 155.

In an example, the communication circuit 120 can wirelessly transmit information to the PG 130. One method of wireless transmission includes acoustic transmission. In an example, information from the communication circuit 120 can be acoustically transmitted to the PG 130 using an ultrasonic transducer 125. Generally, an ultrasonic transducer can emit or receive a sound wave that can travel through mass, such as liquids, gasses, or other elastic medium including tissue. Using ultrasonic communication to transmit PAP information, such as the sensed PAP signal, the conditioned PAP signal, or other PAP information from the PA pressure sensor 110, to the PG 130 allows for low power communication having a minimal interference with the surrounding medium and bodily activity.

In an example, the PAP signal conditioning circuit 115 can be configured to condition the sensed PAP signal for ultrasonic communication, such as by filtering, modulating, or otherwise adapting the sensed PAP signal for ultrasonic communication.

In other examples, the communication circuit 120 can be configured to communicate with or otherwise send or receive information to the PG 130 using other wireless communication methods, such as by using an RF link, the communication circuit 120 can be configured to communicate with the PG 130 using an electrical connection (e.g., hard-wired, etc.) to the PG 130, or the communication circuit 120 can be configured to communicate with the PG 130 using an optical connection.

In an example, the PG 130 can include a RF communication circuit 140, and the diagnostic circuit 150 can include a RF communication circuit 155. The RF communication circuits 140, 155 of the PG 130 and the diagnostic circuit 150 can be configured to allow wireless communicate between or otherwise allow the transfer of information between the PG 130 and the diagnostic circuit 150, such as by using the RF communication link 165.

In the example of FIG. 3, the PG 130 can include an auxiliary physiological sensor 145. In certain examples, the auxiliary physiological sensor 145 can be an implantable medical device external to the PG 130, or the auxiliary physiological sensor 145 can be an external device. The auxiliary physiological sensor 145 can be configured to sense an auxiliary physiological parameter different than the PAP, such as a cardiac signal, a heart rate (HR), an activity signal, a posture signal, a respiration signal, or other physiological parameters. In an example, the auxiliary physiological sensor 145 can be configured to provide a sensed auxiliary physiological signal, such as an electrical, mechanical, or optical sensed auxiliary physiological signal that includes information about the sensed auxiliary physiological parameter of the subject 105.

In the example of FIG. 3, the PG 130 can be configured to receive the sensed auxiliary physiological signal, or other auxiliary physiological parameter information from the auxiliary physiological sensor 145. In an example, the diagnostic circuit 150 can be configured to receive the sensed auxiliary physiological signal, or other auxiliary physiological parameter information, from the PG 130, such as by using the RF communication link 165 or other communication link. In other examples, the auxiliary physiological sensor 145 can be communicatively coupled to the diagnostic circuit 150, and the diagnostic circuit 150 can be configured to receive the sensed auxiliary physiological signal, or other auxiliary physiological parameter information, from the auxiliary physiological sensor 145, without using the PG 130. In certain examples, the diagnostic circuit 150 can be configured to detect an abnormal BP condition using information from the sensed PAP signal and information from the sensed auxiliary physiological signal.

Figure 4:
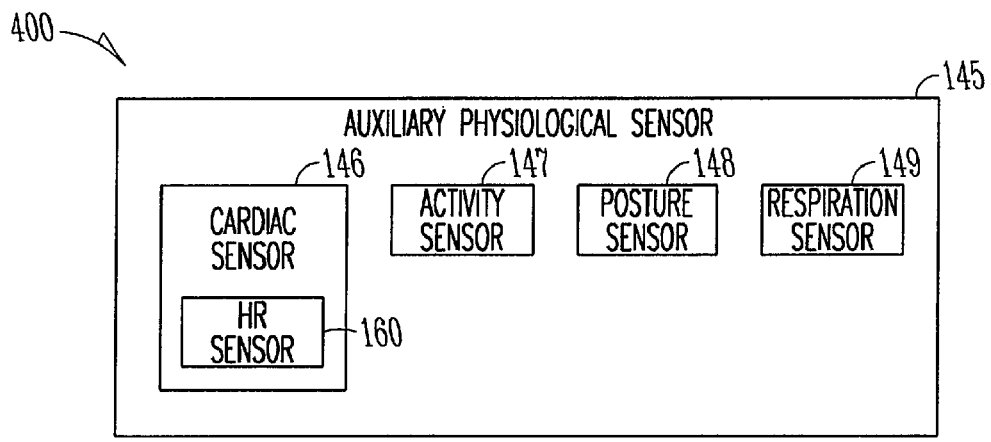
FIG. 4 illustrates generally an example of portions of a system including an auxiliary physiological sensor having a cardiac sensor, an activity sensor, a posture sensor, and a respiration sensor.

FIG. 4 illustrates generally an example of portions of a system 400 including an auxiliary physiological sensor 145 having a cardiac sensor 146, an activity sensor 147, a posture sensor 148, and a respiration sensor 149. Generally, the auxiliary physiological sensor 145 can include at least one of the cardiac sensor 146, the activity sensor 147, the posture sensor 148, or the respiration sensor 149. In certain examples, at least one of the cardiac sensor 146, the activity sensor 147, the posture sensor 148, or the respiration sensor 149, can be an implantable component, an external component, or a combination or permutation of an implantable component and an external component.

In an example, the auxiliary physiological sensor 145 can include a cardiac sensor 146. The cardiac sensor 146 can be configured to sense a cardiac signal of the subject 105 as the auxiliary physiological parameter. The cardiac signal can include any signal indicative of the electrical or mechanical cardiac activity of the heart of the subject 105, e.g., an electrocardiogram (ECG) signal, an impedance signal, an acceleration signal, etc. The cardiac sensor 146 can be configured to provide a sensed cardiac signal, such as an electrical or optical sensed cardiac signal, as the sensed auxiliary physiological signal, that includes information about the cardiac signal of the subject 105. The cardiac sensor 146 can include any device configured to sense the cardiac activity of the subject 105. In certain examples, the cardiac sensor 146 can include an intrinsic cardiac signal sensor, such as one or more than one electrode or lead to sense one or more than one depolarization, or a mechanical sensor, such as an impedance sensor or an accelerometer to sense one or more than one contraction.

In an example, the cardiac sensor 146 can include a heart rate (HR) sensor 160. The HR sensor 160 can be configured to sense a HR of the subject 105 as the auxiliary physiological parameter. The HR of the subject 105 can include any signal indicative of the intrinsic or paced rate of the heart. The HR sensor 160 can be configured to provide a sensed HR signal, such as an electrical or optical sensed HR signal, as the sensed auxiliary physiological signal, that includes information about the sensed HR of the subject 105. The HR sensor 160 can include any device configured to sense the intrinsic or paced HR of the subject 105, such as the cardiac sensor 146.

In an example, the diagnostic circuit 150 can be configured to receive the sensed HR information, such as the sensed HR signal, from the HR sensor 160. In an example, the diagnostic circuit 150 can be configured to determine a relationship between the information from the sensed PAP and the sensed HR. The diagnostic circuit 150 can be configured to determine an abnormal BP condition, including an unstable BP-HR control loop, using the sensed PAP information, such as the sensed PAP signal, and the sensed HR information, such as the sensed HR signal.

In an example, the auxiliary physiological sensor 145 can include an activity sensor 147. The activity sensor 147 can be configured to sense an activity signal of the subject 105 as the auxiliary physiological signal. The activity signal of the subject 105 can include any signal indicative of the activity of the subject 105, such as the amount of subject's present or past motion or rest. The activity sensor 147 can be configured to provide a sensed activity signal, such as an electrical or optical sensed activity signal, as the sensed auxiliary physiological signal, that includes information about the sensed activity of the subject 105. The activity sensor can include any device configured to sense the activity of the subject 105, such as an accelerometer, a minute ventilation (MV) sensor, or other physiological sensor capable of sensing activity.

In an example, the auxiliary physiological sensor 145 can include a posture sensor 148. The posture sensor 148 can be configured to sense a posture signal of the subject 105 as the auxiliary physiological parameter. The posture signal of the subject 105 can include any signal indicative of the posture of the subject, such as the position (e.g., upright, sitting, lying, etc.) of the subject. The posture sensor 148 can be configured to provide a sensed posture signal, such as an electrical or optical sensed posture signal, as the sensed auxiliary physiological signal, that includes information about the sensed posture of the subject 105. The posture sensor can include any device configured to sense the posture of the subject 105, such as an accelerometer to detect the period of rest that can be indicative of sleep state or other period of rest, an impedance sensor, a MV sensor, an electrical axis sensor, or other physiological sensor configured to detect the general position of the subject 105.

In an example, the auxiliary physiological sensor 145 can include a respiration sensor 149. The respiration sensor 149 can be configured to sense a respiration signal of the subject 105 as the auxiliary physiological parameter. The respiration signal can include any signal indicative of the respiration of the subject 105, such as inspiration, expiration, or any combination, permutation, or component of the respiration of the subject 105. The respiration sensor 149 can be configured to provide a sensed respiration signal, such as an electrical or optical respiration signal, as the sensed auxiliary physiological signal, that includes information about the respiration of the subject 105. The respiration sensor 149 can include an implantable sensor including at least one of an accelerometer configured to sense an acceleration indicative of the respiration of the subject 105, an impedance sensor configured to sense an impedance indicative of the respiration of the subject, 105, or a pressure sensor configured to sense a pressure indicative of the respiration of the subject 105. In other examples, the respiration sensor 149 can include other sensors configured to sense the respiration of the subject 105.

Figure 5:
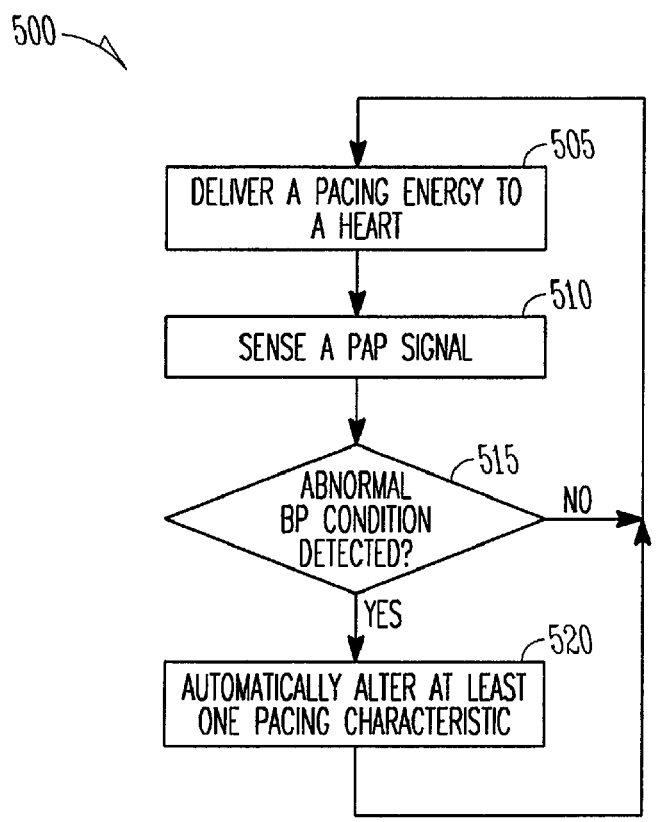
FIG. 5 illustrates generally an example of a method including delivering a pacing energy to a heart, sensing a PAP signal of a PA, and automatically altering at least one pacing characteristic if an abnormal blood pressure (BP) condition is detected.

FIG. 5 illustrates generally an example of a method 500 including delivering a pacing energy to a heart, sensing a PAP signal of a PA, and automatically altering at least one pacing characteristic if an abnormal blood pressure (BP) condition is detected.

At 505, a pacing energy, or other electrical stimulation signal adapted to provide a cardiac stimulation therapy, is delivered to a heart. The pacing energy can be delivered to the heart using at least one pacing characteristic, such as at least one of a pacing rate, a pacing waveform (e.g., amplitude, frequency, phase, shape, etc.), an atriventricular (AV) delay, an interventricular (VV) delay, a pacing mode, or a pacing site. In an example, the pacing energy can be delivered using the PG 130.

At 510, a PAP signal of a PA is sensed and a sensed PAP signal is provided. In an example, the PAP signal can be sensed and the sensed PAP signal can be provided using the PA pressure sensor 110.

At 515, if an abnormal BP condition is detected, then, at 520, at least one pacing characteristic can be automatically altered in response to the detected abnormal BP condition. At 515, if an abnormal BP condition is not detected, then the at least one pacing characteristic is not automatically altered and the process flow continues to 505.

At 515, the abnormal BP condition is detected using the sensed PAP signal. In an example, the abnormal BP condition can be detected by monitoring the PAP for changes or signals indicative of an abnormal BP condition, including various clinical types of hypertension (e.g., chronic hypertension, transient hypertension, nocturnal hypertension, circadian hypertension, systolic hypertension, diastolic hypertension, or other clinical types of hypertension) or hypotension (chronic hypotension, transient hypotension, circadian hypotension, or other clinical types of hypotension). In certain examples, the monitoring the PAP can be accomplished over short periods of time (e.g., hours), or longer periods of time (e.g., days, weeks, months, or years). The sensed PAP signal can be recorded and monitored for trends indicative of abnormal BP conditions. In an example, the sensed PAP signal can be monitored periodically (e.g., recorded once per hour, once per day, etc.), or the sensed PAP signal can be monitored continuously. In an example, the abnormal BP condition can be detected using the diagnostic circuit 150.

In certain examples, at 515, various changes, trends, or other characteristics of the sensed PAP signal can be indicative of certain abnormal BP conditions. For example, a high BP value over a certain period of time (e.g., days, months, or longer) can be indicative of chronic hypertension. In another example, an upward trend compared to an established BP baseline across a positive gradient threshold can be indicative of transient hypertension. A low BP value over a certain period of time can be indicative of chronic hypotension. A downward trend compared to the established BP baseline across a negative gradient threshold can be indicative of transient hypotension. A high BP during night time, during sleep, or during other periods of rest can be indicative of nocturnal hypertension.

In an example, the sensed PAP signal can be conditioned into a conditioned PAP signal for transmission, and the conditioned PAP signal can be transmitted, such as transmitted to the diagnostic circuit 150. In an example, the transmitting the conditioned PAP signal can include acoustically transmitting the conditioned PAP signal using at least one ultrasonic transducer or other device capable of acoustic transmission. In other examples, the transmitting the conditioned PAP signal can include other types of transmission, such as RF or other wireless transmission.

At 520, the at least one pacing characteristic can be automatically altered, e.g., in response to the detected abnormal BP condition at 515. If, at 515, hypertension is detected, then, at 520, the at least one pacing characteristic can be automatically altered to alleviate the detected hypertension, such as by altering the at least one pacing characteristic to promote a more efficient pumping of the heart. In an example, if hypertension is detected, then the pacing rate can be decreased. If the cardiac output is high, e.g., such as during hypertension, then the AV delay can be modified (e.g., shortened or lengthened, depending on the individual subject's condition) to reduce the cardiac output or contractility. In other examples, the pacing mode can be switched (e.g., to one or a combination of at least one of rate, AV/VV timing, site, capture voltage, etc.) to reduce the cardiac output.

If, at 515, hypotension is detected, then, at 520, the at least one pacing characteristic can be automatically altered to alleviate the detected hypotension, such as by altering the at least one pacing characteristic to induce the heart to pump less efficiently, increase the cardiac output, or otherwise alleviate the detected hypotension. In an example, if hypotension is detected, then a pacing therapy with a controlled pacing rate can be applied to maintain the BP in the subject's normal range. The pacing rate can be modulated to accommodate subject-specific conditions, such as respiratory sinus arrhythmia or other condition. In an example, multiple or different poles could be paced in order to increase the stroke volume. In other examples, the pacing rate can be modulated and multiple or different poles can be paced.

At 520, after the at least one pacing characteristic is automatically altered, then, at 505, the pacing energy can be delivered to the heart using the at least one altered pacing characteristic.

Figure 6:
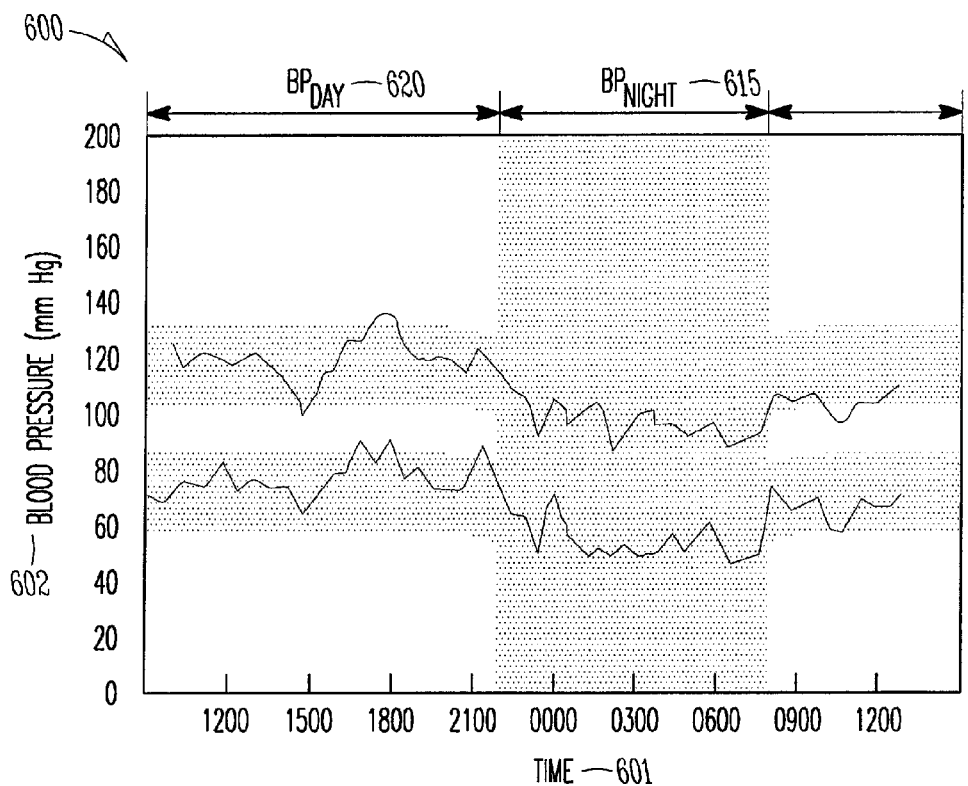
FIG. 6 illustrates generally an example of a relationship between Blood Pressure and Time.

FIG. 6 illustrates generally an example of a relationship 600 between Blood Pressure 602 and Time 601. Relationship 600 illustrates a typical circadian pattern of a normal subject, showing the daytime BP, $BP_{day}$ 620, and the nighttime BP, $BP_{night}$ 615. Generally, the average nighttime BP of a subject is lower than the average daytime BP of a subject. Nocturnal hypertension occurs where the BP fails to fall (e.g., at least 20 mm Hg) at night. Nocturnal hypertension can be a marker for greater risk of renal and cardiovascular complications, correlate with other conditions, such as sleep apnea, or end organ damage. Using the PA pressure sensor 110 to monitor the PAP of the subject can allow for detection of nocturnal hypertension or other chronic or short-term hypotension or hypertension conditions without requiring constant or frequent long-term physician monitoring (e.g., by a sleep-study or other hospitalization).

Figure 7:
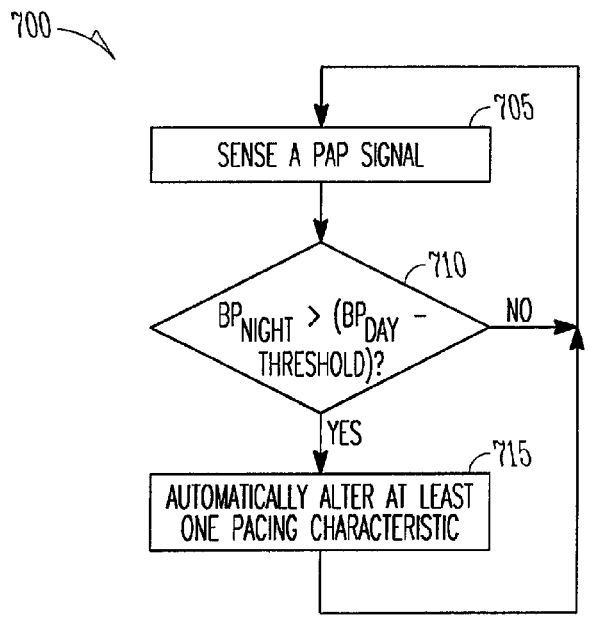
FIG. 7 illustrates generally an example of portions of a method including sensing a PAP signal of a PA and automatically altering at least one pacing characteristic if the nighttime BP is greater than the daytime BP minus a threshold.

FIG. 7 illustrates generally an example of portions of a method 700 including sensing a PAP signal of a PA and automatically altering at least one pacing characteristic if the daytime BP is greater than the nighttime BP by at least a threshold.

At 705, a PAP signal of a PA is sensed and a sensed PAP signal is provided. In an example, the PAP signal can be sensed and the sensed PAP signal can be provided using the PA pressure sensor 110.

At 710, if the daytime BP does not exceed the nighttime BP by at least a threshold, then, at 715, at least one pacing characteristic is automatically altered. At 710, if the daytime BP exceeds the nighttime BP by the threshold, then the at least one pacing characteristic is not automatically altered and the process flow continues to 705.

At 710, the nighttime BP can be detected using the sensed PAP signal. In an example, the nighttime BP can be determined using a clock, such as by setting an absolute nighttime interval (e.g., from 12:00 a.m. until 6:00 a.m., from 11:00 p.m. until 6:00 a.m., etc.). Similarly, at 710, the daytime BP can be detected using the sensed PAP signal. In an example, the daytime BP can be determined using a clock, such as by setting an absolute time interval (e.g., from 6:00 a.m. until 12:00 a.m., from 6:00 a.m. until 11:00 a.m., etc.). In an example, the nighttime BP can be compared to the daytime BP using a comparator, a processor, or other device, such as the diagnostic circuit 150. In certain examples, the absolute nighttime or daytime interval can be set using data from the subject, such as the subject's normal sleeping pattern. In other examples, the nighttime or daytime interval can be set using information from other sensors, such as an activity sensor or a posture sensor, as the awake state of the subject can be determined using the information about the patient's activity or posture.

A high nighttime BP can include any BP value within a threshold of the daytime BP and can be indicative of various physiological conditions, including nocturnal hypertension. In an example, the threshold can include an absolute threshold or a variable threshold. In certain examples, the threshold can be set at a value of 20 mm Hg, a value of greater than 20 mm Hg (e.g., 25 mm Hg), or a value of less than 20 mm Hg (e.g., 15 mm Hg). In an example, the threshold can be set using a clinical circadian pattern, such as that disclosed in FIG. 6, or the threshold can be set using a patient-specific, or a population-specific, circadian pattern.

At 715, the at least one pacing characteristic can be automatically altered, e.g., in response to the detected nighttime BP. If, at 710, the daytime BP does not exceed the nighttime BP by at least the threshold, then, at 715, the at lest one pacing characteristic can be automatically altered to alleviate the physiological condition (e.g., nocturnal hypertension), such as by altering the at least one pacing characteristic to promote a more efficient pumping of the heart. In an example, if the comparison of the nighttime BP and the daytime BP is indicative of nocturnal hypertension (e.g., if the daytime BP does not exceed the nighttime BP by the threshold), then at least one of the pacing rate can be decreased (e.g., decreased by an amount, such as 10 paces per minute (ppm), 15 ppm, etc., or decreased by a percentage or a function of the current pacing rate), the AV delay can be modified (e.g., decreased or increased (depending on the individual subject's condition) by an amount, such as 20 ms, 25 ms, etc., or decreased or increased (depending on the individual subject's condition) by a percentage or a function of the current AV delay), or the VV delay can be modified (e.g., increased or decreased (depending on the individual subject's condition) by an amount, such as 20 ms, 25 ms, etc., or increased or decreased (depending on the individual subject's condition) by a percentage or a function of the current VV delay).

Figure 8:
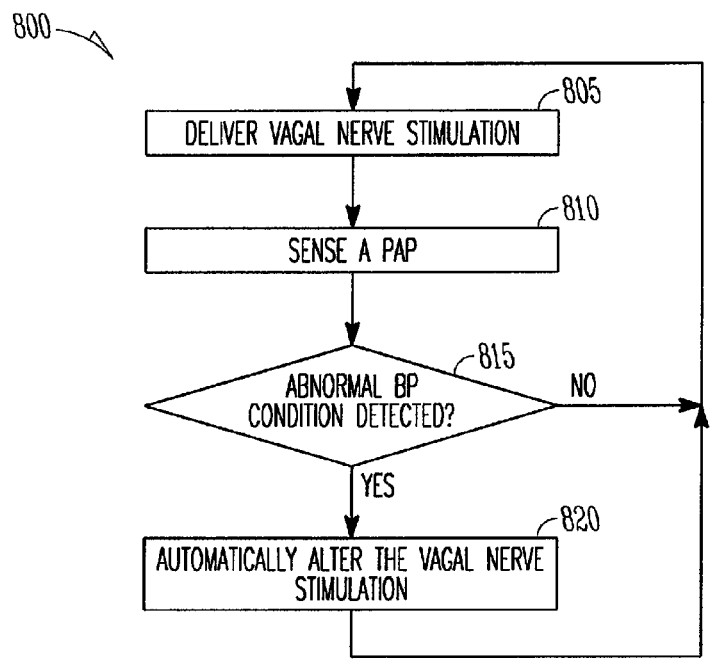
FIG. 8 illustrates generally an example of portions of a method including delivering vagal nerve stimulation, sensing a PAP of a PA, and automatically altering the vagal nerve stimulation if an abnormal BP condition is detected.

FIG. 8 illustrates generally an example of portions of a method 800 including delivering vagal nerve stimulation, sensing a PAP of a PA, and automatically altering the vagal nerve stimulation if an abnormal BP condition is detected.

At 805, vagal nerve stimulation can be delivered. In an example, the vagal nerve stimulation can be delivered using the PG 130.

At 810, a PAP signal of a PA is sensed and a sensed PAP signal is provided. In an example, the PAP signal can be sensed and the sensed PAP signal can be provided using the PA pressure sensor 110.

At 815, if an abnormal BP condition is detected, then, at 820, the vagal nerve stimulation can be automatically altered in response to the detected abnormal BP condition. At 815, if an abnormal BP condition is not detected, then the vagal nerve stimulation is not automatically altered and the process flow continues to 805.

At 820, the vagal nerve stimulation can be automatically altered, e.g., in response to the detected abnormal BP condition at 815. If, at 815, hypertension is detected, then, at 820, the vagal nerve stimulation can be automatically altered to alleviate the detected hypertension, such as by altering the vagal nerve stimulation to promote a more efficient pumping of the heart. In an example, if hypertension is detected, then the stimulation rate can be decreased, or other stimulation characteristics can be modulated to decrease the cardiac output, decrease the HR, or alleviate the detected hypertension.

If, at 815, hypotension is detected, then, at 820, the vagal nerve stimulation can be automatically altered to alleviate the detected hypotension, such as by altering the vagal nerve stimulation to induce the heart to pump less efficiently, increase the cardiac output, or otherwise alleviate the detected hypotension. In an example, if hypotension is detected, then the stimulation rate can be increased, or other stimulation characteristics can be modulated to increase the cardiac output, increase the HR, or alleviate the detected hypotension.

At 820, after the at least one pacing characteristic is automatically altered, then, at 805, the vagal nerve stimulation can be delivered using the altered vagal nerve stimulation.

Figure 9:
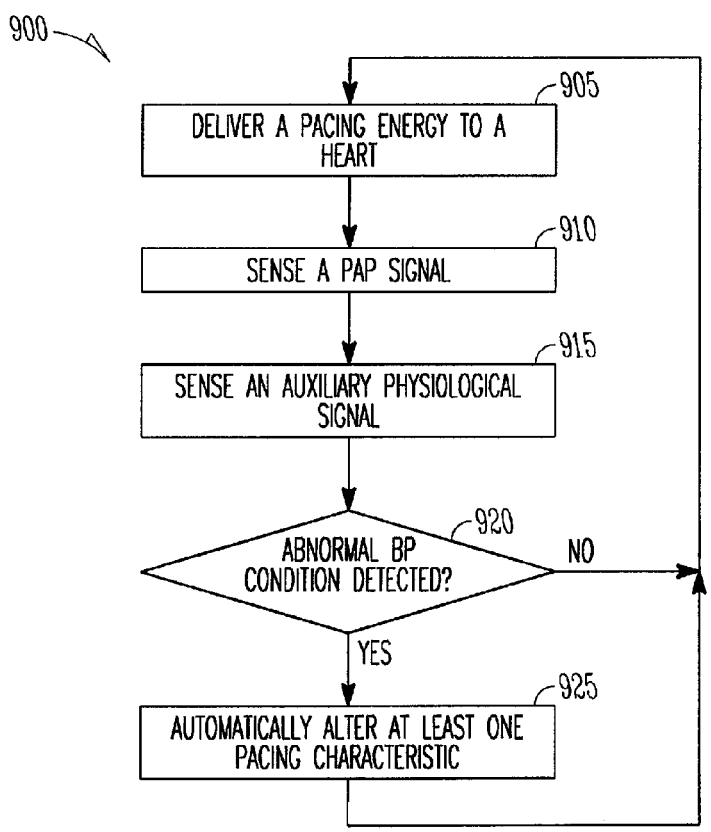
FIG. 9 illustrates generally an example of portions of a method including delivering a pacing energy to a heart, sensing a PAP signal of a PA, sensing an auxiliary physiological signal, and automatically altering at least one pacing characteristic if an abnormal BP condition is detected.

FIG. 9 illustrates generally an example of portions of a method 900 including delivering a pacing energy to a heart, sensing a PAP signal of a PA, sensing an auxiliary physiological signal, and automatically altering at least one pacing characteristic if an abnormal BP condition is detected.

At 905, a pacing energy can be delivered to a heart. In an example, the pacing energy can be delivered using the PG 130.

At 910, a PAP signal of a PA is sensed and a sensed PAP signal is provided. In an example, the PAP signal can be sensed and the sensed PAP signal can be provided using the PA pressure sensor 110.

At 915, an auxiliary physiological signal of the subject is sensed and a sensed auxiliary signal is provided. In an example, at least one of a cardiac signal, a HR, an activity signal, a posture signal, or a respiration signal can be sensed as the auxiliary physiological signal. In certain examples, only a cardiac signal is sensed. In other examples, an activity signal and a posture signal can be sensed. In an example, the auxiliary physiological signal of the subject can be sensed and the sensed auxiliary signal can be provided using the auxiliary physiological sensor 145.

At 920, if an abnormal BP condition is detected, then, at 925, at least one pacing characteristic can be automatically altered in response to the detected abnormal BP condition. At 920, if an abnormal BP condition is not detected, then the at least one pacing characteristic is not automatically altered and the process flow continues to 905.

At 920, the abnormal BP condition can be detected using at least one of the sensed PAP signal or the sensed auxiliary physiological signal. In an example, the abnormal BP condition can be detected by monitoring at least one of the PAP for changes or signals indicative of an abnormal BP condition or the auxiliary physiological signal for changes or signals indicative of an abnormal BP condition. In certain examples, the monitoring of the auxiliary physiological signal can be concurrent with that of the PAP, or the monitoring of the auxiliary physiological signal can occur at different times than that of the PAP.

In an example, the sensed auxiliary physiological signal can be used to adjust for BP effect due to activity or posture artifacts. In an example, the automatically altering the at least one pacing characteristic in response to the detected abnormal BP condition can be turned off when the BP trend or characteristics, or other PAP information, are consistent with the sensed auxiliary physiological signal information (e.g., periods of moderate to strenuous activity, etc.). In other examples, the sensed PAP signal, when combined with the sensed cardiac signal (e.g., a sensed ECG signal), can be used to distinguish between systolic and diastolic hypertension.

In certain examples, the PAP can be synchronized with the auxiliary physiological signal to measure the coupling of the auxiliary physiological signal and the PAP. In an example, the PAP can be synchronized with the sensed HR to measure or trend the coupling of the HR and the PAP. The coupling of the HR and the PAP can be indicative of an unstable BP-HR control loop. In an example, the HR-PAP coupling can be computed as a time-varying coherence and can indicate the covariability of the HR and the BP. In an example, the diagnostic circuit 150 can provide a notification of the unstable BP-HR control loop to a user for further diagnosis or therapy.

In other examples, a notification of the detected abnormal BP condition, or other detected physiological condition, can be provided to the subject, to the user, or to another device, such as an external programmer or repeater. In certain examples, the notification can be provided to the user via email or other communication, or the notification can be provided to the subject using an audible notification (e.g., a buzz, bell, or other sound) or a mechanical notification (e.g., a vibration).

The above description is intended to be illustrative, and not restrictive. For example, in the examples of FIG. 1-9, various examples, including delivering a pacing energy to a heart, sensing a PAP signal of a PA, detecting an abnormal BP condition, automatically altering at least one pacing characteristic, delivering vagal nerve stimulation, automatically altering the vagal nerve stimulation, sensing an auxiliary physiological signal, and providing a notification are disclosed. It is to be understood that the disclosed examples are not exclusive and can be implemented either alone, in combination, or in various permutations or combinations. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
an implantable pulmonary artery (PA) pressure sensor configured to sense a pulmonary artery pressure (PAP) of a PA and provide a sensed PAP signal of a patient;
a diagnostic circuit configured to detect an abnormal blood pressure (BP) condition providing a differential indication of non-sleep vs. sleep hypertension by:
  determining a sleep interval using at least one of (1) time-of-day information or (2) patient status information indicating whether the patient is sleeping;
  determining a sleep BP using information from at least a portion of the sensed PAP signal during the sleep interval;
  determining a non-sleep BP using information from at least a portion of the sensed PAP signal outside of the sleep interval;
  determining the differential indication of non-sleep vs. sleep hypertension by comparing information about the sleep BP to information about the non-sleep BP; and an implantable pulse generator (PG) configured to deliver a pacing energy to a heart and automatically alter at least one pacing characteristic in response to the detected abnormal BP condition providing the differential indication of non-sleep vs. sleep hypertension.

2. The system of claim 1, wherein the PA pressure sensor is configured to be fixed to a location within the PA.

3. The system of claim 1, wherein the abnormal BP condition includes hypertension, including at least one of chronic hypertension, transient hypertension, systolic hypertension, or diastolic hypertension.

4. The system of claim 1, wherein the abnormal BP condition provides the differential indication of non-sleep vs. sleep hypertension by providing an indication of nocturnal hypertension.

5. The system of claim 1, wherein the at least one pacing characteristic includes at least one of a pacing rate, a pacing waveform, an atrioventricular (AV) delay, an interventricular (VV) delay, a pacing mode, or a pacing site.

6. The system of claim 1, wherein the PG is further configured to deliver vagal nerve stimulation and automatically alter the vagal nerve stimulation in response to the detected abnormal BP condition.

7. The system of claim 1, wherein the PG includes the diagnostic circuit.

8. The system of claim 1, wherein the diagnostic circuit includes an external programmer and the PG is configured to wirelessly communicate with the external programmer.

9. The system of claim 1, including:
a PAP signal conditioning circuit configured to condition the sensed PAP signal into a conditioned PAP signal; and
a communication circuit configured to transmit the conditioned PAP signal to the PG.

10. The system of claim 9, wherein the communication circuit includes an ultrasonic transducer configured to acoustically transmit the conditioned PAP signal to the PG and the PAP signal conditioning circuit is configured to condition the sensed PAP signal for the acoustic transmission.

11. The system of claim 1, wherein the PG includes a radio frequency (RF) communication circuit and the diagnostic circuit is configured to communicate to the PG using an RF communication link.

12. The system of claim 1, including:
an auxiliary physiological sensor configured to sense an auxiliary physiological parameter different than the PAP and provide a sensed auxiliary physiological signal; and
wherein the diagnostic circuit is configured to detect an abnormal BP condition using information from the sensed PAP signal and information from the sensed auxiliary physiological signal.

13. The system of claim 12, wherein the auxiliary physiological sensor includes a cardiac sensor, configured to sense a cardiac signal as the auxiliary physiological parameter.

14. The system of claim 13, wherein the cardiac sensor includes a heart rate (HR) detector, configured to sense a HR; and
wherein the diagnostic circuit is configured to determine a relationship between the information from the sensed PAP signal and the sensed HR signal, and the abnormal BP condition includes an unstable BP-HR control loop.

15. The system of claim 12, wherein the auxiliary physiological sensor includes at least one of an activity sensor, a posture sensor, or a respiration sensor.

16. The system of claim 1, wherein the abnormal BP condition provides the differential indication of non-sleep vs. sleep hypertension by providing an indication of non-sleep hypertension.

17. The system of claim 1, wherein the abnormal BP condition provides the differential indication of non-sleep vs. sleep hypertension by comparing information about the sleep BP to information about the non-sleep BP using a threshold, and wherein the differential indication of non-sleep vs. sleep hypertension provides an indication of sleep hypertension when the non-sleep BP fails to exceed the sleep BP by a specified threshold amount.

18. A method comprising:
sensing a pulmonary artery pressure (PAP) and providing a sensed PAP signal;
determining an abnormal blood pressure (BP) condition using information from the sensed PAP signal including:
determining a sleep interval using at least one of (1) time-of-day information or (2) patient status information indicating whether the patient is sleeping;
determining a sleep BP using information from at least a portion of the sensed PAP signal during the sleep interval;
determining a non-sleep BP using information from at least a portion of the sensed PAP signal outside of the sleep interval; and
determining a differential indication of non-sleep vs. sleep hypertension by comparing information about the sleep BP to information about the non-sleep BP;
delivering pacing energy to a heart; and
automatically altering at least one pacing characteristic in response to the detected abnormal BP condition.

19. The method of claim 18, wherein the sensing includes using an implantable pulmonary artery (PA) pressure sensor configured to be fixed to a location within a PA.

20. The method of claim 18, wherein the detecting the abnormal BP condition includes detecting hypertension, including detecting at least one of chronic hypertension, transient hypertension, systolic hypertension, or diastolic hypertension.

21. The method of claim 18, wherein the detecting the abnormal BP condition includes determining the differential indication of non-sleep vs. sleep hypertension to provide an indication of nocturnal hypertension.

22. The method of claim 18, wherein the detecting the abnormal BP condition includes determining the differential indication of non-sleep vs. sleep hypertension to provide an indication of awake hypertension.

23. The method of claim 18, wherein the automatically altering the at least one pacing characteristic includes automatically altering at least one of a pacing rate, a pacing waveform, an atrioventricular (AV) delay, an interventricular (VV) delay, a pacing mode, or a pacing site.

24. The method of claim 18, including:
delivering vagal nerve stimulation; and
automatically altering the vagal nerve stimulation in response to the detected abnormal BP condition.

25. The method of claim 18, wherein the detecting the abnormal BP condition includes using a diagnostic circuit, the method further including:
conditioning the sensed PAP signal into a conditioned PAP signal for transmission to the diagnostic circuit; and
transmitting the conditioned PAP signal to the diagnostic circuit.

26. The method of claim 25, wherein the using the diagnostic circuit includes using an ultrasonic transducer, the conditioning the sensed PAP signal for transmission includes conditioning the PAP signal for acoustic transmission, and the transmitting the conditioned PAP signal includes acoustically transmitting the conditioned PAP signal.

27. The method of claim 18, including:
sensing an auxiliary physiological parameter different than the PAP and providing a sensed auxiliary physiological signal; and
wherein the detecting the abnormal BP condition includes using information from the sensed PAP signal and information from the sensed auxiliary physiological signal.

28. The method of claim 27, wherein the sensing the auxiliary physiological parameter includes sensing a cardiac signal.

29. The method of claim 28, wherein the sensing the cardiac signal includes sensing a heart rate (HR); the method further including determining a relationship between the sensed PAP information and the sensed HR, wherein the detecting the abnormal BP condition includes detecting an unstable BP-HR control loop.

30. The method of claim 27, wherein the sensing the auxiliary physiological signal includes sensing at least one of an activity signal, a posture signal, or a respiration signal.

31. A system comprising:
an implantable pulmonary artery (PA) pressure sensor configured to sense a pulmonary artery pressure (PAP) of a PA of a subject and to provide a sensed PAP signal;
a PAP signal conditioning circuit configured to condition the sensed PAP signal into a conditioned PAP signal for acoustic transmission;
a communication circuit including an ultrasonic transducer configured to acoustically transmit the conditioned PAP signal to an implantable pulse generator (PG);
an external diagnostic circuit including a radio frequency (RF) communication circuit configured to receive the conditioned PAP signal from the implantable PG, wherein the external diagnostic circuit is configured to detect an abnormal blood pressure (BP) condition including a differential indication of non-sleep vs. sleep hypertension using:
a determination of a sleep interval using at least one of (1) time-of-day information or (2) patient status information indicating whether the patient is sleeping;
information from at least a portion of the conditioned PAP signal during the sleep interval, including a sleep BP;
information from at least a portion of the conditioned PAP signal during the non-sleep interval, including a non-sleep BP; and
a threshold;
wherein the external diagnostic circuit is configured to detect the differential indication of non-sleep vs. sleep hypertension if the non-sleep BP fails to exceed the sleep BP by at least the threshold; and
wherein the implantable PG includes an ultrasonic transducer configured to receive the conditioned PAP signal from the communication circuit and an RF communication circuit configured to transmit the conditioned PAP signal to the external diagnostic circuit, wherein the implantable PG is configured to deliver a pacing energy to a heart and to automatically alter at least one pacing characteristic in response to the detected abnormal BP condition.

* * * * *

UNITED STATES PATENT AND TRADEMARK OFFICE
CERTIFICATE OF CORRECTION

| | |
|---|---|
| PATENT NO. | : 8,027,724 B2 |
| APPLICATION NO. | : 11/833435 |
| DATED | : September 27, 2011 |
| INVENTOR(S) | : Xuan Wei et al. |

Page 1 of 1

It is certified that error appears in the above-identified patent and that said Letters Patent is hereby corrected as shown below:

On the face page, in field (57), under "Abstract", in column 1, line 11, delete "atriventricular" and insert -- atrioventricular --, therefor.

Signed and Sealed this
Tenth Day of January, 2012

David J. Kappos
*Director of the United States Patent and Trademark Office*